United States Patent [19]

Böger et al.

[11] 4,233,306
[45] Nov. 11, 1980

[54] 1-IMINOMETHYLENE-SUBSTITUTED 2-(PHENOXY-ALKYL)-2-IMIDOAZOLINE DERIVATIVES

[75] Inventors: Manfred Böger, Weil am Rhein, Fed. Rep. of Germany; Jozef Drabek, Oberwil, Switzerland; Günter Mattern, Liestal, Switzerland; Walter Traber, Reinach, Switzerland

[73] Assignee: Ciba-Geigy Corporation, Ardsley, N.Y.

[21] Appl. No.: 63,239

[22] Filed: Aug. 3, 1979

[30] Foreign Application Priority Data

Aug. 14, 1978 [CH] Switzerland .......................... 8631/78
Mar. 8, 1979 [CH] Switzerland .......................... 2250/79
Jul. 3, 1979 [CH] Switzerland .......................... 6194/79

[51] Int. Cl.³ .................. C07D 233/22; C07D 401/12; C07D 417/12
[52] U.S. Cl. .................................... 424/263; 424/270; 424/273 R; 542/414; 542/424; 548/342; 548/353
[58] Field of Search .............. 542/414, 424; 548/342, 548/353; 424/263, 270, 273 R

[56] References Cited

U.S. PATENT DOCUMENTS 4,163,105  7/1979  Wysong ..................... 548/342

OTHER PUBLICATIONS

Copp et al., Chem. Abst. 89 (1978) #109497.
Copp et al., Chem. Abst. 89 (1978) #109498.

Primary Examiner—Arthur P. Demers
Attorney, Agent, or Firm—John J. Maitner

[57] ABSTRACT

Compounds of the formula I

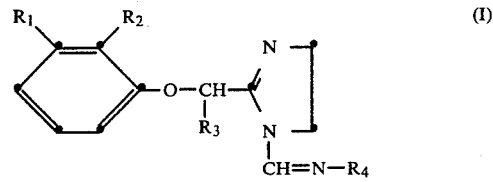

wherein $R_1$ and $R_2$ are each chlorine or methyl, $R_3$ is hydrogen or $C_1$-$C_4$-alkyl and $R_4$ is cyano or a group of the formula A or B.

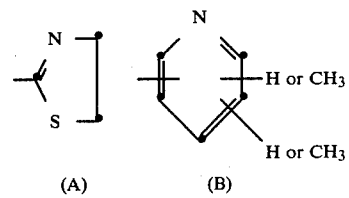

(A)     (B)

and their acid addition salts possess useful pesticidal in particular acaricidal properties.

10 Claims, No Drawings

1-IMINOMETHYLENE-SUBSTITUTED 2-(PHENOXY-ALKYL)-2-IMIDOAZOLINE DERIVATIVES

The present invention relates to novel 1-iminomethylene-substituted 2-(phenoxy-alkyl)-2-imidazoline derivatives which have an action against insect pests, to processes for producing these derivatives, to insecticidal compositions containing them as active ingredients, and to processes for the control of insect pests by application of the novel compounds.

2-(Phenoxy-alkyl)-2-imidazoline derivatives having a pesticidal action, particularly an ectoparasiticidal action, are known (see for example South African patent application No. 78/2449, Japanese Patent Publication No. 76/106739, and German Offenlegungsschriften Nos. 2,756,638 and 2,756,639). According to the present invention, there are provided novel compounds of this type, which likewise have an action against insect pests, especially against representatives of the order Acarina, and which, by virtue of their advantageous biological properties, are particularly suitable for practical application, The novel 1-iminomethylene-substituted 2-(phenoxy-alkyl)-2-imidazoline derivatives according to the invention correspond to the formula I

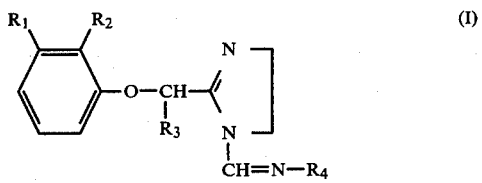

wherein
$R_1$ and $R_2$ are, independently of each other, a chlorine atom or a methyl group,
$R_3$ is a hydrogen atom or a $C_1$–$C_4$-alkyl group, and
$R_4$ is a cyano group or a group of the formula A or B

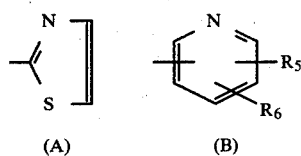

wherein $R_5$ and $R_6$ are, independently of each other, a hydrogen atom or a methyl group.

Alkyl groups denoted by $R_3$ are the methyl, ethyl, n-propyl, i-propyl, n-butyl, i-butyl, sec-butyl and t-butyl group.

Preferred types of substituents and combinations of these among each other in the compounds of the formula I are as follows:

(1) for $R_1$ and $R_2$: at the same time methyl or at the same time chlorine;
(2) for $R_3$: hydrogen or ethyl, especially ethyl;
(3) for $R_4$: a group of the formula B, particularly a group of the formula B'

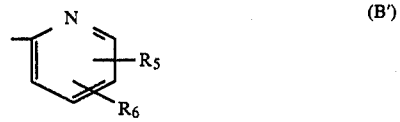

in which $R_5$ and $R_6$ are each hydrogen or methyl.

The compounds of the formula I also occur in the form of acid addition salts, for example mineral salts, and can be used according to the invention in the form of their salts. Accordingly, both the free compounds of the formula I and their acid addition salts come within the scope of the present invention.

It has now been shown that surprisingly the compounds of the formula I according to the invention have a valuable action both against acarids which damage plants (mites: e.g. of the families Tetranychidae, Tarsonemidae, Eriophyidae, Tyroglyphidae and Glycyphagidae) and against ectoparasitic acarids (mites and ticks: e.g. of the families Ixodidae, Argasidae, Sarcoptidae and Dermanyssidae), which harm productive animals. Furthermore, it is now established that these acaricidal properties are coupled with a toxicity to warm-blooded animals that is favourable for practical application, by virtue of which the compounds of the formula I, and the acid addition salts thereof which are nontoxic to warm-blooded animals, are particularly suitable for controlling pests of the order Acarina in cultivated crops of useful plants and ornamental plants, as well as for controlling ectoparasitic ticks and mites on productive animals.

The compounds of the formula I are produced by processes analogous to known processes, for example by reacting a compound of the formula II

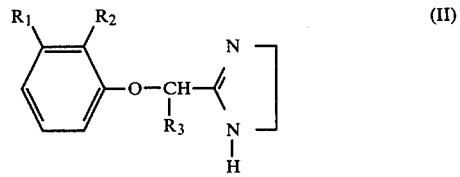

with a compound of the formula III

with $R_1$, $R_2$, $R_3$ and $R_4$ in the formulae II and III having the meanings already defined under the formula I, and $R_7$ being a methyl or ethyl group.

The process is performed advantageously at a temperature of between $-20°$ and $120°$ C., under normal or slightly elevated pressure, and preferably in the presence of a solvent or diluent inert to the reactants. Suitable solvents or diluents are for example ethers and ethereal compounds, such as diethyl ether, diisopropyl ether, dioxane and tetrahydrofuran; aromatic hydrocarbons, such as benzene, toluene and xylenes; and ketones such as acetone, methyl ethyl ketone and cyclohexanone.

The compounds of the formula I produced in this manner can be converted by methods known per se into their acid salts.

The compounds of the formula I in which $R_3$ is an alkyl group occur in the form of optically active isomers. If therefore optically active starting materials are not used in the production process, there are necessarily obtained racemic mixtures. Isomeric mixtures of this kind can be separated for example by chromatographical separating methods into the individual isomeric forms. The scope of the present invention embraces both the individual optically active isomers and mixtures thereof.

The starting materials employed in the process described in the foregoing are known (see South African patent application No. 78/2449 and German Offenlegungsschrift No. 2,756,638) or they can be produced by methods analogous to known methods.

The compounds of the formula I are used according to the invention on their own, or they form a constituent of compositions which also contain suitable carriers or additives or mixtures of such substances. Suitable carriers and additives can be solid or liquid and they correspond to the substances common in formulation practice, such as natural or regenerated substances, solvents, dispersing agents, wetting agents, adhesives, thickeners, binders and/or fertilisers.

The acaricidal action of the compositions according to the invention can be considerably broadened by the addition of other acaricides and/or insecticides. Suitable additives are for example: organic phosphorus compounds; nitrophenols and derivatives thereof; formamidines; ureas; pyrethrin-like compounds; carbamates and chlorinated hydrocarbons.

The compositions according to the invention can be in the form of dusts, granulates, dispersions, solutions and suspensions, as well as in the form of water-dispersible wettable powders, pastes, emulsions and emulsion concentrates, and can be applied in these forms.

The content of active substance (compound of the formula I) in the compositions described above is between 0.1 and 95%; it is to be mentioned in this connection that with application from an aeroplane, or by means of other suitable application devices, also higher concentrations can be used.

The active substances of the formula I can be formulated for example as follows:

EMULSION CONCENTRATE I 20 parts by weight of the above-mentioned active substance are dissolved in 70 parts by weight of xylene, and to the solution are added 10 parts by weight of an emulsifying agent consisting of a mixture of an arylphenylpolyglycol ether and the calcium salt of dodecylbenzenesulfonic acid.

Water can be added in any proportion to the emulsion concentrate to form a milky emulsion.

EMULSION CONCENTRATE II 5 to a maximum of 30 parts by weight of active substance are dissolved at room temperature, with stirring, in 30 parts by weight of dibutylphthalate, 10 parts by weight of Solvent 200 (low-viscous, highly aromatic petroleum distillate), 15 to 35 parts by weight of Dutrex 238 FC (viscous highly aromatic petroleum distillate), and to the solution are added 10 parts by weight of an emulsifier mixture consisting of castor-oil polyglycol ether and the calcium salt of dodecylbenzenesulfonic acid.

The emulsion concentrate thus obtained produces milky emulsions when water is added.

WETTABLE POWDER 5 to 30 parts by weight of the active substance are thoroughly mixed, in a mixing apparatus, with 4 parts by weight of an absorbing carrier material (Kieselsäure K 320 [silicic acid] or Wessalon S) and 55 to 80 parts by weight of a carrier material (bolus alba or Kaolin B 24) and a dispersing agent mixture consisting of 5 parts by weight of a sodium lauryl sulfonate and 5 parts by weight of an alkyl-aryl-polyglycol ether.

This mixture is ground to 5–15 μm in a dowelled disc mill or air jet mill. A good suspension is obtained by adding water to the wettable powder thus produced.

DUST 5 parts by weight of finely ground active substance are thoroughly mixed with 2 parts by weight of a precipitated silicic acid and 93 parts by weight of talc.

POUR-ON SOLUTION

| | |
|---|---|
| active substance | 30.0 g |
| sodium dioctylsulfosuccinate | 3.0 g |
| benzyl alcohol | 48.0 g |
| peanut oil | 19.8 g |
| | 100.8 g = 100 ml |

The active substance is dissolved in the benzyl alcohol with stirring and if necessary with slight heating. The sodium dioctylsulfosuccinate and peanut oil are added to the solution, and are dissolved with heating and thorough stirring.

The Examples which follow serve to further illustrate the invention.

EXAMPLE 1

Production of 1-[N-(2-pyridyl)-formimino]-2-[1-(2,3-dimethylphenoxy)-propyl]-2-imidazoline To a solution of 11.6 g of 2-[1-(2,3-dimethylphenoxy)-propyl]-2-imidazoline of the formula

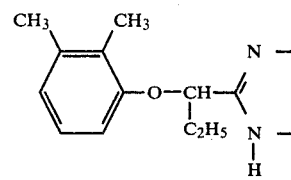

in 100 ml of toluene was added 7.5 g of N-(2-pyridyl)-formiminoethyl ether of the formula

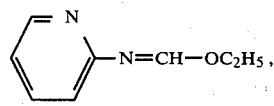

and the reaction mixture was stirred for 12 hours at 70° C. The solution obtained was subsequently concentrated by evaporation, and the residue was recrystallised from toluene/hexane. There was obtained in this manner 1-[N-(2-pyridyl)-formimino]-2-[1-(2,3-dimethylphenoxy)-propyl]-2-imidazoline of the formula (Compound No. 1)

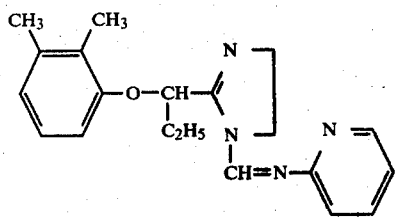

in the form of white powder having a melting point of 108°–110° C.

Also the following compounds of the formula I were produced by a process analogous to the production process described in the foregoing:

| Compound No. | Structure | m.p. |
|---|---|---|
| 2. | (2,3-dimethylphenoxy)-CH₂-imidazoline-CH=N-C≡N | m.p. 172°–173° C. |
| 3. | (2,3-dimethylphenoxy)-CH₂-imidazoline-CH=N-(thiazole) | m.p. 160°–162° C. |
| 4. | (2,3-dimethylphenoxy)-CH₂-imidazoline-CH=N-(6-methylpyridin-2-yl) | m.p. 144°–146° C. |
| 5. | (2,3-dimethylphenoxy)-CH₂-imidazoline-CH=N-(4-methylpyridin-2-yl) | m.p. 138°–140° C. |
| 6. | (2,3-dimethylphenoxy)-CH₂-imidazoline-CH=N-(3-methylpyridin-2-yl) | m.p. 99°–101° C. |
| 7. | (2,3-dimethylphenoxy)-CH(C₂H₅)-imidazoline-CH=N-(4-methylpyridin-2-yl) | m.p. 88°–90° C. |

-continued
| Compound No. | | |
|---|---|---|
| 8. | 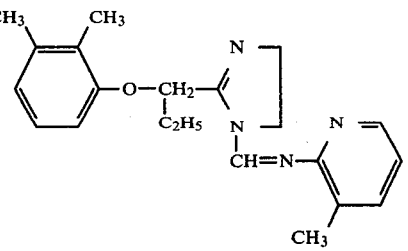 | m.p. 98°–100° C. |
| 9. | 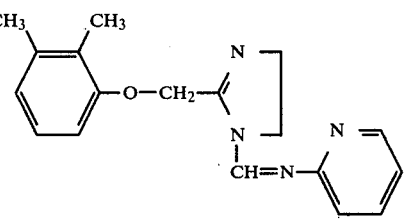 | m.p. 140°–142° C. |
| 10. | 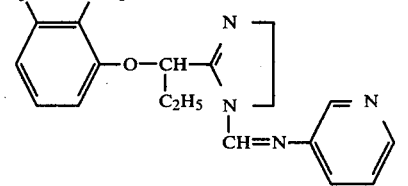 | m.p. 101°–102° C. |
| 11. | 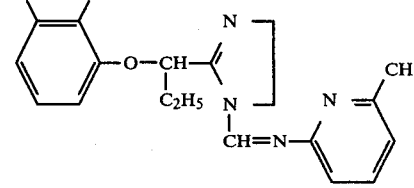 | m.p. 126°–128° C. |
| 12. | 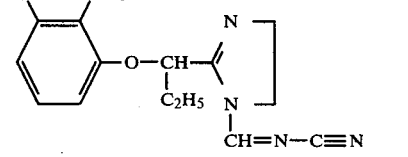 | m.p. 130°–132° C. |
| 13. | 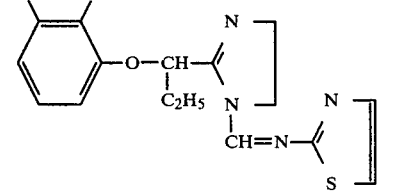 | m.p. 78°–80° C. |
| 14. | 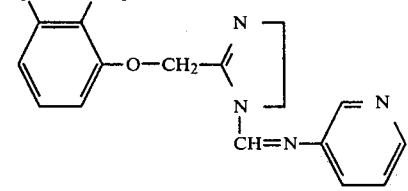 | m.p. 104°–106° C. |

-continued

| Compound No. | | |
|---|---|---|
| 15. | 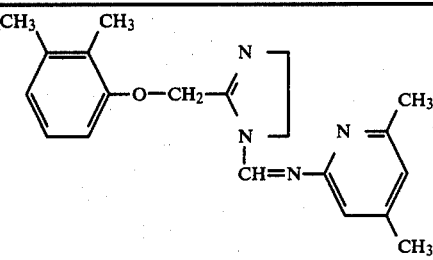 | m.p. 131°–133° C. |
| 16. | 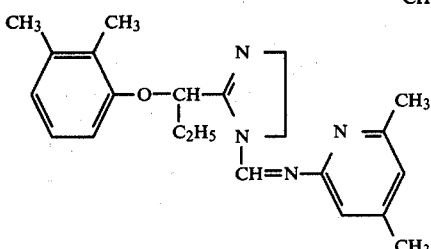 | m.p. 105°–106° C. |
| 17. | 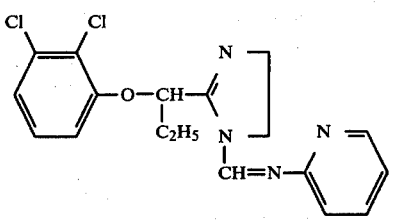 | m.p. 81°–83° C. |
| 18. | 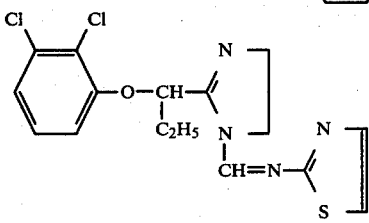 | m.p. 96°–98° C. |
| 19. | 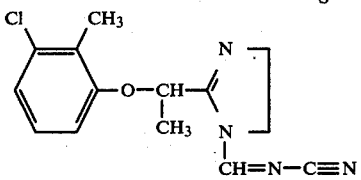 | m.p. 130°–132° C. |
| 20. | 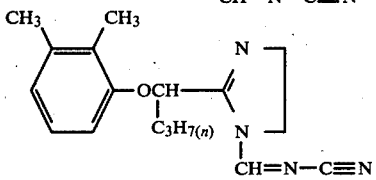 | m.p. 130°–131° C. |

EXAMPLE 2

Action against plant-damaging acarids: *Tetranychus urticae* (OP-sensitive) and *Tetranychus cinnabarinus* (OP-tolerant)

The primary leaves of *Phaseolus vulgaris* plants were infested, 16 hours before the test for acaricidal action, with an infested piece of leaf from a mass culture of *Tetranychus urticae* (OP-sensitive) and *Tetranychus cinnabarinus* (OP-tolerant), respectively, (tolerance is with respect to diazinon compatibility).

The plants infested in this manner were subsequently sprayed until dripping wet with a test solution containing 400 and 200 ppm, respectively, of the compound to be tested. An assessment was made after 24 hours and again after 7 days, by examination of the imagines and larvae (all mobile stages) under a binocular microscope, of the number of living and dead individuals, respectively.

One plant was used per concentration and per test species. The plants were standing in greenhouse compartments at 25° C. during the course of the test.

Compounds according to Example 1 exhibited in this test a favourable action against individuals of the species *Tetranychus urticae* and *Tetranychus cinnabarinus*.

EXAMPLE 3

Action against *ectoparasitic acarids:* (ticks) *Rhipicephalus bursa* (imagines and larvae), *Amblyomma hebraeum* (♀ imagines, nymphs and larvae) and *Boophilus microplus* (larvae-OP-sensitive and OP-tolerant)

The test objects used were larvae (in each case about 50), nymphs (in each case about 25) and imagines (in each case about 10) of the trick species *Rhipicephalus bursa*, *Amblyomma hebraeum* and *Boophilus microplus*. The test insects were immersed for a short time in an aqueous emulsion or solution containing 0.1; 1.0; 10; 50 or 100 ppm of the compound to be tested.

The emulsions or solutions in the test tubes were then absorbed with cotton wool, and the wetted test insects were left in the test tubes treated in this manner.

An evaluation of the degree of destruction obtained at each concentration was made after 3 days for larvae and after 14 days for nymphs and imagines.

Compounds according to Example 1 exhibited in this test a good action against larvae, nymphs and imagines of the species *Rhipicephalus bursa* and *Amblyomma hebraeum* and also against larvae (OP-resistant and OP-sensitive) of the species Boophilus microplus.

What is claimed is:

1. A compound of the formula I (I)

[Structure: benzene ring with $R_1$, $R_2$ substituents, $-O-CH(R_3)-$ linked to a 5-membered N-containing ring, with $N-CH=N-R_4$]

wherein $R_1$ and $R_2$ are, independently of each other, chlorine or methyl, $R_3$ is hydrogen or $C_1-C_4$-alkyl and $R_4$ is cyano or a group of the formula A or B (A)   (B)

[Structures of groups A (thiazole) and B (pyrimidine with $R_5$, $R_6$)]

wherein $R_5$ and $R_6$ are, independently of each other, hydrogen or methyl, and the acid addition salts thereof.

2. A compound as claimed in claim 1 wherein $R_4$ is a group of the formula B'

(B')

[Structure of group B' with $R_5$, $R_6$]

wherein $R_5$ and $R_6$ have the meanings given in claim 1.

3. A compound as claimed in claim 1 or 2 wherein $R_6$ is hydrogen.

4. A compound as claimed in claim 1 or 2 wherein $R_1$ and $R_2$ are both chlorine or both methyl and $R_3$ is hydrogen or ethyl.

5. A compound as claimed in claim 1 or 2 wherein $R_1$ and $R_2$ are both chlorine or both methyl and $R_3$ is ethyl.

6. A compound as claimed in claim 1 of the formula

[Structure: 2,6-dimethylphenoxy-CH($C_2H_5$)- linked to imidazole with CH=N-pyrimidine-$CH_3$]

7. A compound as claimed in claim 1 of the formula

[Structure: 2,6-dimethylphenoxy-CH($C_2H_5$)- linked to imidazole with CH=N-pyrimidine-$CH_3$]

8. An acaricidal agent comprising an acaricidally effective amount of a compound as claimed in claim 1 together with an inert, solid or liquid diluent or carrier therefor.

9. A method of controlling representatives of the order Acarina at a locus, which method comprises applying to said locus an acaricidally effective amount of a compound as claimed in claim 1.

10. A method as claimed in claim 9 wherein the locus is an agricultural or horticultural crop.

* * * * *